United States Patent
Domash et al.

(10) Patent No.: US 7,484,769 B2
(45) Date of Patent: Feb. 3, 2009

(54) CONNECTOR TO CASSETTE INTERFACE SYSTEM

(75) Inventors: David M. Domash, Irvine, CA (US); James J. Foster, Santa Ana, CA (US)

(73) Assignee: Alcon, Inc., Hunenberg (CH)

( * ) Notice: Subject to any disclaimer, the term of this patent is extended or adjusted under 35 U.S.C. 154(b) by 330 days.

(21) Appl. No.: 11/487,842

(22) Filed: Jul. 17, 2006

(65) Prior Publication Data

US 2008/0058727 A1    Mar. 6, 2008

(51) Int. Cl.
*A61M 39/00* (2006.01)

(52) U.S. Cl. .................. 285/124.4; 285/401; 604/30; 29/890.09

(58) Field of Classification Search .......... 285/93, 285/401, 402, 124.3, 124.4, 124.5, 124.2, 285/209, 328, 330, 331, 914; 604/242, 30, 604/118, 29; 29/890.09
See application file for complete search history.

(56) References Cited

U.S. PATENT DOCUMENTS

| | | | | |
|---|---|---|---|---|
| 978,504 A * | 12/1910 | Stewart | ..................... | 285/209 |
| 4,150,673 A * | 4/1979 | Watt | ........................... | 604/408 |
| 4,211,439 A * | 7/1980 | Moldestad | ................... | 285/27 |
| 4,280,723 A * | 7/1981 | Moldestad | ................... | 285/376 |
| 4,619,640 A * | 10/1986 | Potolsky et al. | ................ | 604/7 |
| 5,201,717 A * | 4/1993 | Wyatt et al. | ................. | 604/192 |
| 5,267,956 A * | 12/1993 | Beuchat | ....................... | 604/30 |
| 5,499,969 A * | 3/1996 | Beuchat et al. | .............. | 604/30 |
| 5,538,405 A * | 7/1996 | Patno et al. | ................... | 417/326 |
| 5,725,511 A * | 3/1998 | Urrutia | ....................... | 604/533 |
| 5,947,937 A * | 9/1999 | Urrutia et al. | .............. | 604/533 |
| 5,989,423 A * | 11/1999 | Kamen et al. | ................. | 604/30 |
| 6,319,223 B1 * | 11/2001 | Wortrich et al. | .............. | 604/30 |
| 6,402,207 B1 * | 6/2002 | Segal et al. | ................. | 285/330 |
| 7,115,228 B2 * | 10/2006 | Lundtveit et al. | ............. | 422/44 |
| 2006/0081258 A1* | 4/2006 | Nalagatla et al. | ....... | 128/207.18 |

* cited by examiner

*Primary Examiner*—David E Bochna
(74) *Attorney, Agent, or Firm*—W. David Lee

(57) ABSTRACT

The disclosed connector to cassette interface system includes a set of individual keyed connectors having a shroud on the lower portion. The perimeter of each shroud includes an array of tabs or protrusions keyed to one of a corresponding array of skirted portals in the cassette cover. The tabs or protrusions on the shroud portion of each individual keyed connector may further serve to prevent rotation of each connector beyond about 60°.

16 Claims, 7 Drawing Sheets

CONNECTOR TO CASSETTE INTERFACE SYSTEM

FIELD

The present invention pertains to the connection of sources of fluid to a piece of medical/surgical equipment; more particularly, the present invention pertains to a system for mounting connectors to a cassette assembly used with a piece of medical/surgical equipment.

BACKGROUND

Many pieces of medical/surgical equipment are built to manage the flow of a set of different fluids associated with the performance of certain medical/surgical procedures. Such fluids may include air, liquid irrigation fluids, liquid antibiotics, blood, or in the case of eye surgery, tissue that has been removed and aspirated from the eye via a probe or handpiece. Typically, the conduit for such fluids in a piece of medical/surgical equipment is a section of silicone tubing. Those setting up a piece of medical/surgical equipment for a particular medical/surgical procedure connect individual sections of silicone tubing, one to another, to assure that the needed fluids are placed where they need to be at the proper time during the medical/surgical procedure.

Connection of silicone tubing sections, one to another, is accomplished using a variety of different types of fittings. One of the more popular types of fittings used with silicone tubing sections in medical/surgical equipment is a luer fitting. In a luer fitting a tapered male luer fitting engages a similarly tapered female luer fitting. The male and female luer fittings may be held together by a set of internally and externally threaded connectors which surround the male and female luer fittings once they have been mated together. When the male and female tapered luer fittings have been mated together and the threaded connectors have been threadably engaged together around the male and female luer fittings, a secure connection is made between two sections of silicone tubing permitting the leak-free flow of a fluid therethrough.

Because different sets of fluids are associated with each procedure that can be performed with a piece of medical/surgical equipment, some pieces of medical/surgical equipment use replaceable manifolds or cassettes to facilitate the grouping of the necessary tubing connections. In this manner, the appropriate set of fluids needed to perform a selected medical/surgical procedure from the set of available medical/surgical procedures enabled by a piece of medical/surgical equipment is provided.

To distinguish between connections when multiple tubing connections are placed close to one another, engineers and designers of medical/surgical equipment typically use different sizes of luer fittings. However, engineers and designers quickly run out of luer fitting size options when multiple types of fluids are used.

The existing problem of properly mating a plurality of luer fittings together with the limited number of luer fitting connection sizes available has been solved in the prior art by the use of silicone tubing sleeves which are used during the pre-connection process. In one particular prior art solution, pre-attached silicone tubing sleeves have been used to attach bottle spike tubing to a manifold or cassette used with a piece of medical/surgical equipment while maintaining the male luer geometry. Pre-attached prior art silicone tubing sleeves are used primarily to provide stress relief for the connections to silicone tubing sections and to enable pre-attachment of prior art silicone tubing sections to the manifolds or cassettes used in medical/surgical equipment.

It has been found that prior art pre-attached silicone tubing sleeves are costly and difficult to incorporate into the automated manufacture of medical/surgical equipment. In addition, prior art silicone tubing sleeves are difficult to place over the recessed fittings located in the manifold or cassette assembly. Prior art silicone tubing sleeves are also not as simple to remove and reapply as typical luer fittings. Further, pre-attached prior art silicone tubing sleeves cannot be aseptically connected to the manifold or cassette assembly.

There are additional drawbacks to the pre-attached prior art silicone tubing sleeves. Some pre-attached prior art silicone tubing sleeves cannot endure the rigors of shipping. Pre-attached prior art silicone tubing sleeves do not allow for physical lockout of a connector when an improper connection with a manifold or cassette assembly is attempted.

It is well known that improper or cross connection of fluids to a piece of medical/surgical equipment presents a patient safety issue and can result in the creation of a dangerous condition. Accordingly, a need remains in the art for a connector to cassette assembly interface system that can be used to facilitate the set up of a piece of medical/surgical equipment for a particular medical/surgical procedure. The connector to cassette assembly interface system should provide secure connectors for luer fittings, provide a lockout if an improper connection is attempted, and protect the male and female portions of the luer fitting from contamination.

SUMMARY

The connector to cassette assembly interface system of the present invention provides secure connections for luer fittings, provides a lockout if an improper connection is attempted, and protects the male and female portions of the luer fitting from contamination.

The disclosed connector to cassette assembly interface system includes a manifold or cassette assembly having a cover portion and a body portion. The cover portion of the manifold or cassette assembly includes a plurality of skirted portals formed on its underside. Aligned with the skirted portals are a plurality of tubular openings formed in the body portion of the manifold or cassette assembly.

Mating with the individual skirted portals formed on the underside of the cover portion of the manifold or cassette assembly are a set of individual keyed connectors. Each individual keyed connector has an upper portion and a lower portion. The lower portion of each individual keyed connector has a luer fitting surrounded by a shroud. The exterior surface of the shroud contains a unique surface configuration which acts a key portion whose shape is tied to the type of fluid flowing through the connector. Specifically, the key portion on the bottom of the lower portion of the shroud includes a set of protrusions which match a set of corresponding recesses formed in each skirted portal. By matching the set of protrusions extending outwardly from the shroud with the set of recesses in each skirted portal in the cover portion of the manifold or cassette assembly, the health care professional connecting the sections of silicone tubing used to transport the set of needed fluids to the piece of medical/surgical equipment can assure that the connectors only enter the cassette assembly at the proper predetermined locations for the needed fluids.

The upper portion of each individual keyed connector preferably includes finger engagement wings for manually rotating the keyed connector once the keyed connector has been inserted into the skirted portal formed in the cover portion of the manifold or cassette assembly.

BRIEF DESCRIPTION OF THE DRAWING FIGURES

A better understanding of the connector to cassette interface system of the present invention may be had by reference to the drawing figures, wherein.

DESCRIPTION OF THE EMBODIMENTS

It is the purpose of the disclosed invention to provide a connector to cassette interface system that has the following features:

1) A lock-out system for use when connecting a set of silicone tubing sections to a manifold or cassette assembly which uses an array of unique key geometries on each connector to remove the risk of cross connection between tubing sections. Specifically:
   a) A set of tabs or protrusions extending from the lower portion of each connector which provide a unique key geometry to assure proper connection of a tubing section with a port on a manifold or cassette assembly;
   b) A connection portion on each connector which allows a health care professional to manually grasp each connector and easily plug the connector into the manifold or cassette assembly without contaminating the fittings portion.
2) Aseptic mounting of a set of keyed connectors to a manifold or cassette assembly. Specifically:
   a) A shroud having a diameter sufficient to surround the luer fitting;
   b) A shroud having a length to prevent touch contamination of the luer fitting.

While the disclosed connector to cassette interface system has been designed for use with an ophthalmic surgical system, those of ordinary skill in the art will understand that the disclosed connector to cassette assembly interface system may be used with a wide variety of different types of medical/surgical equipment which require connections to predetermined sets of fluids for proper performance of one or more procedures.

Figure 1:
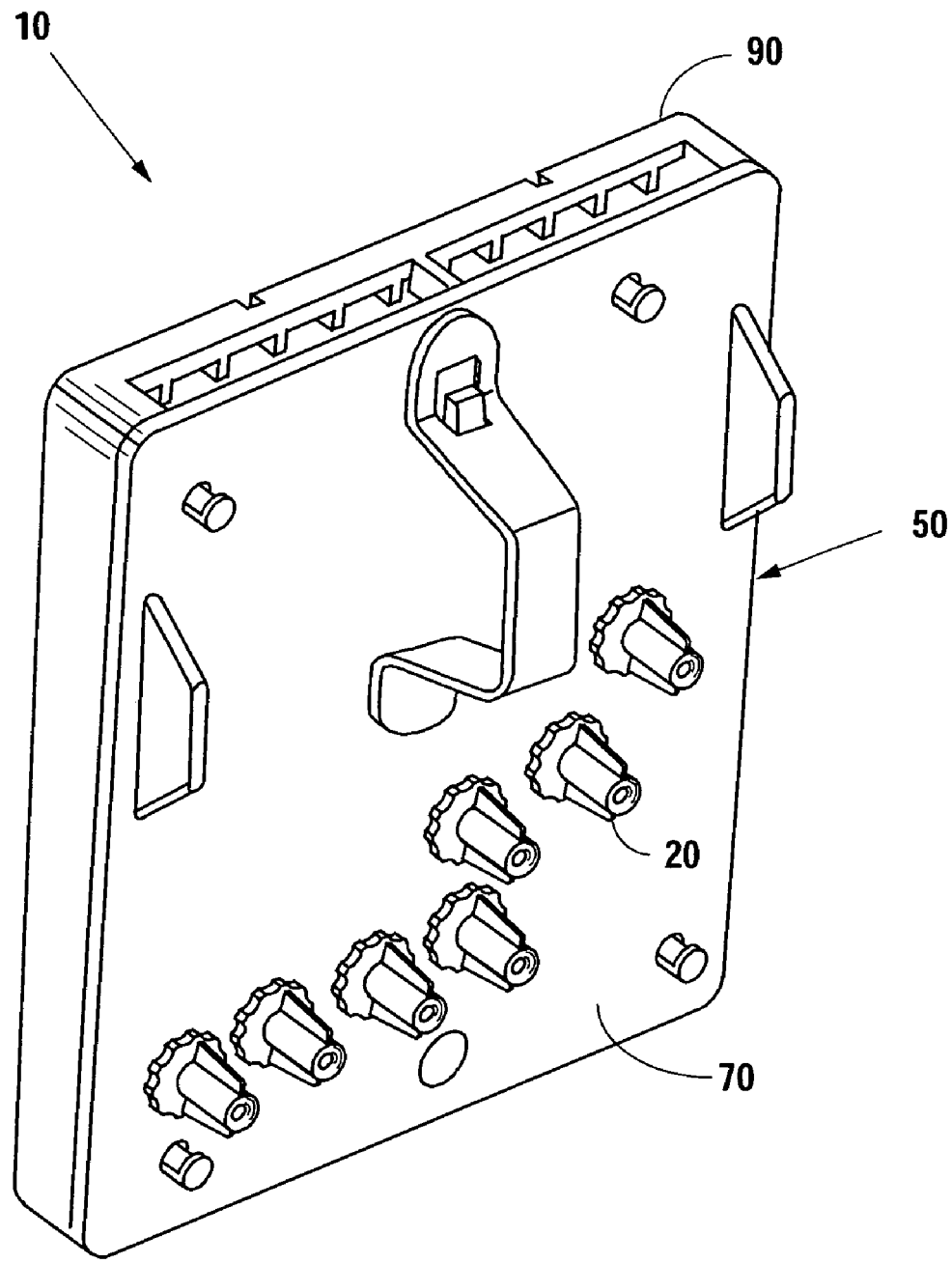
FIG. 1 is a perspective view of a manifold or cassette assembly together with a set of connectors.
Figure 2A:
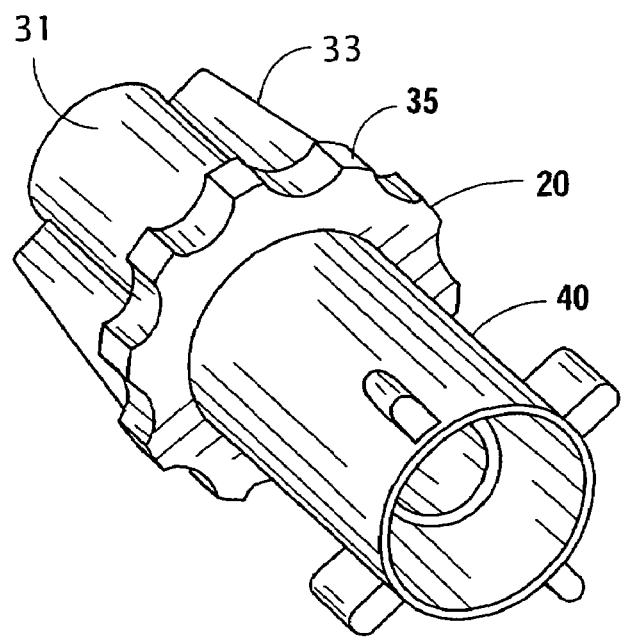
FIG. 2A is a perspective view of a keyed connector showing a luer fitting within the lower portion.
Figure 2B:
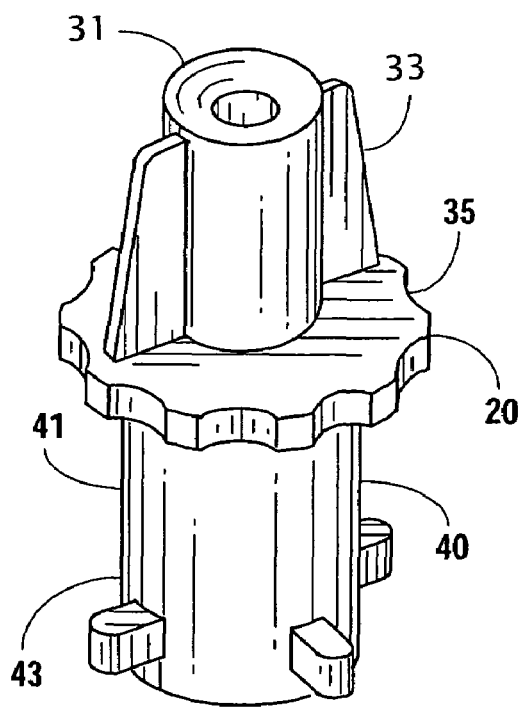
FIG. 2B is a perspective view of the keyed connector illustrated in FIG. 2A showing its upper portion.
Figure 3:
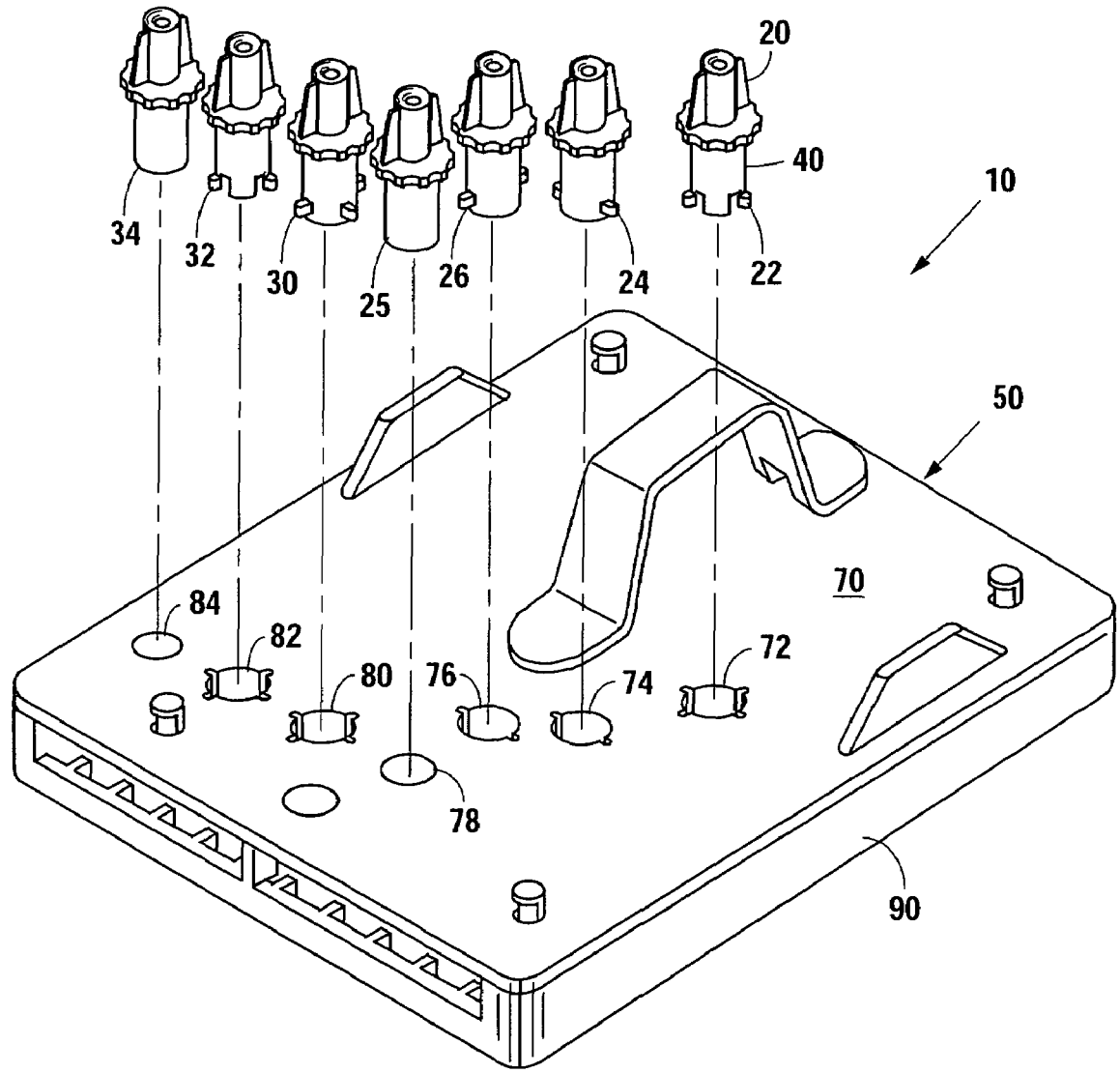
FIG. 3 is an exploded view of the manifold or cassette assembly together with the set of keyed connectors as shown in FIG. 1.
Figure 4B:
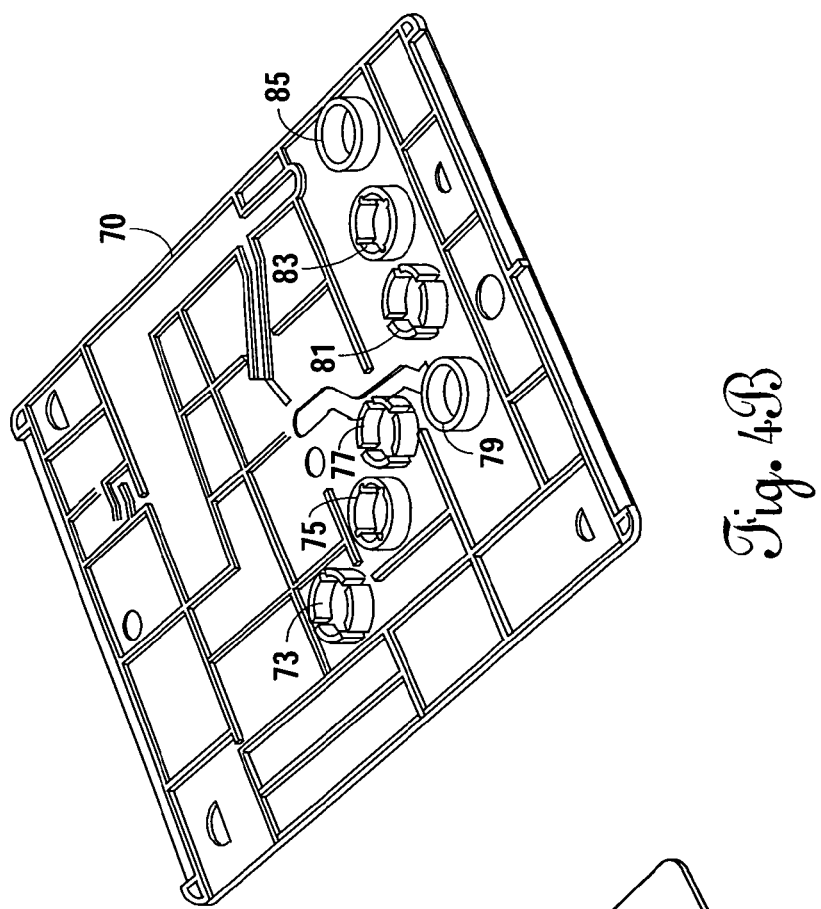
FIG. 4B is a perspective view of the bottom of the cover portion of the manifold or cassette assembly.
Figure 4A:
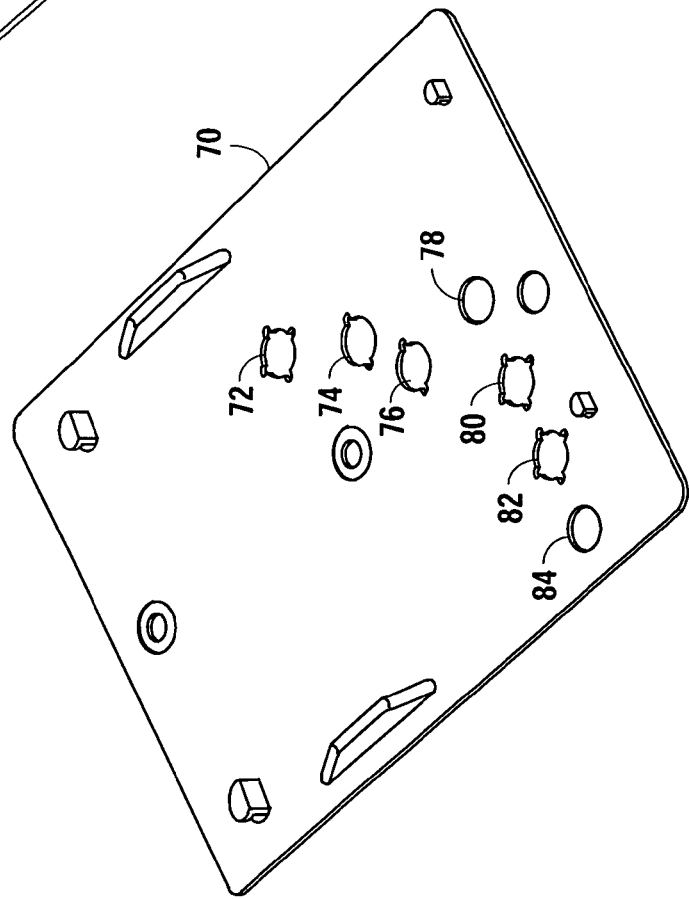
FIG. 4A is a perspective view of the top of the cover portion of the manifold or cassette assembly.
Figure 4C:
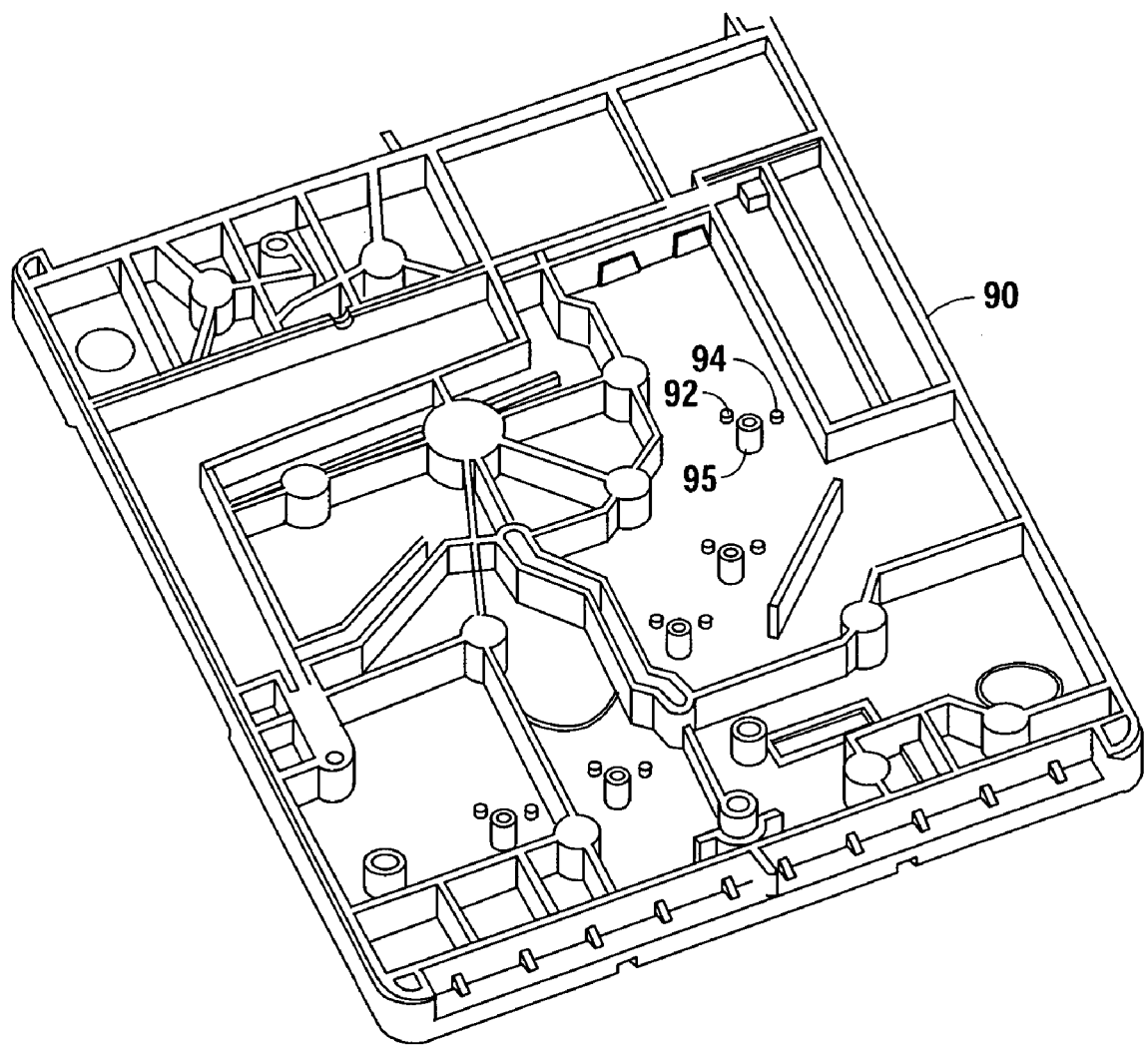
FIG. 4C is a perspective view of the body portion of the manifold or cassette assembly.
Figure 5:
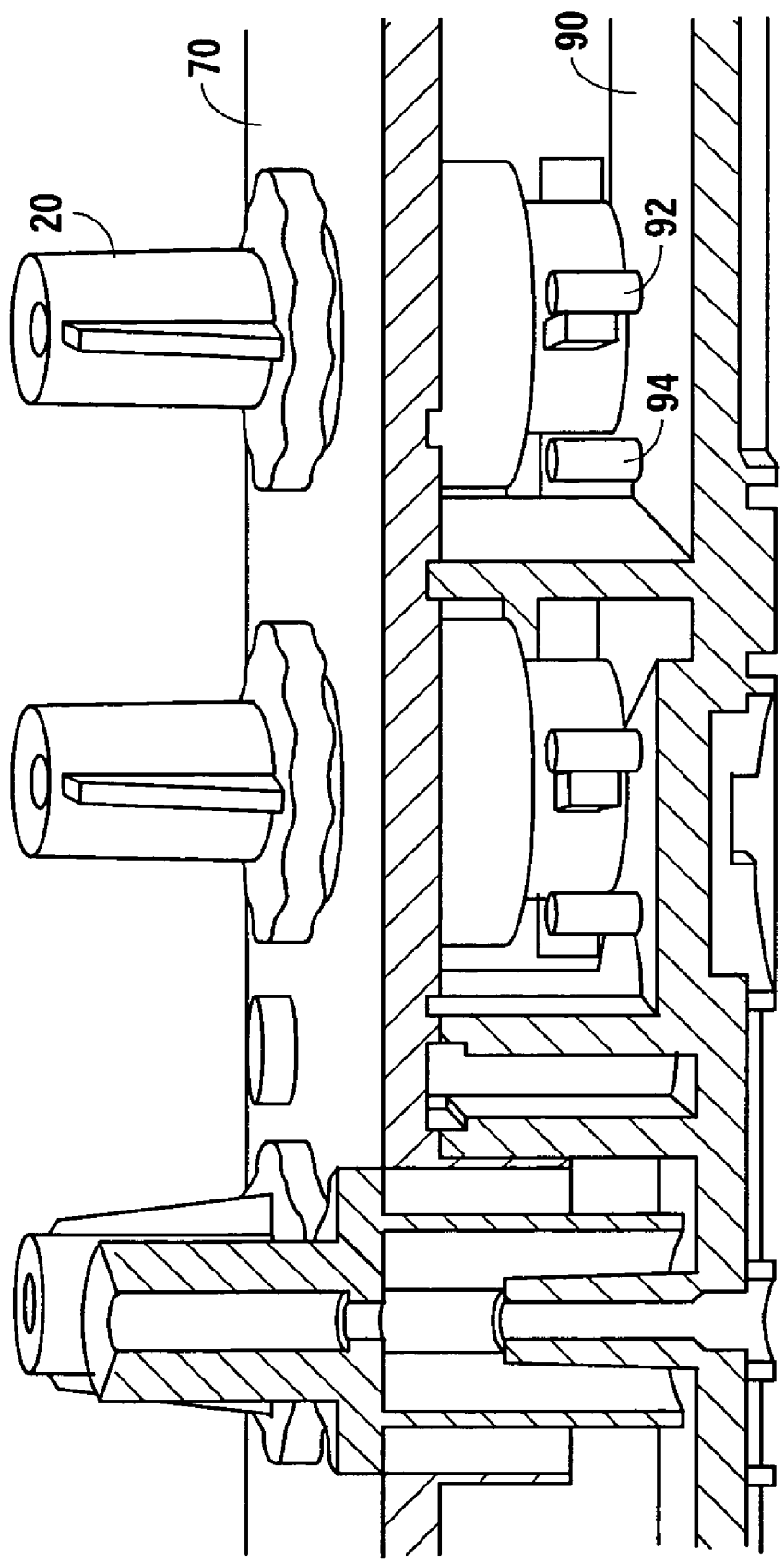
FIG. 5 is a perspective view, in partial section, showing a set of individual connectors mounted in the manifold or cassette assembly.

The connector to cassette interface system 10 which meets the purposes described above appears in FIG. 1. The general design of each individual keyed connector 20 appears in FIGS. 2A and 2B. FIG. 3 is an exploded view showing the mounting of individual connectors 20 into the manifold or cassette assembly 50. Once the individual connectors are inserted through the skirted portals in the cover portion 70 of the manifold or cassette assembly 50 into the body portion 90 of the manifold or cassette assembly 50, they are preferably turned about 60° to a position where they contact either forward stops 92 or back stops 94 formed in the body portion 90 of the manifold or cassette assembly 50 as shown in FIGS. 4C and 5.

To assure proper interfitment of the keyed connectors 20 with the manifold or cassette assembly 50, the connectors 20 are designed to have a variety of different individual key designs formed around the outer surface of the bottom of the shroud 40 as shown in FIG. 3. The arrangement of the array of extensions, protrusions, or tabs 22, 24, 26, 28, 30, 32, 34 on the shroud 40 create various key configurations. Shroud 40 length and shroud 40 diameter may also used to create various shroud 40 key configurations. While substantially circular shrouds are shown in the preferred embodiment, those of ordinary skill in the art will understand that the upper portion 41 of the shroud can be circular and the lower portion 43 of the shroud 40 can be formed to have straight sides as in a triangle, rectangle, pentagon, etc.

The array of openings or portals 72, 74, 76, 78, 80, 82, 84 which form the key features on the cassette assembly 50 together with the skirts 73, 75, 77, 79, 81, 83, 85 under each opening 72, 74, 76, 78, 80, 82, 84 prevent misconnection of tubing sets to the cassette assembly 50. Although in a preferred embodiment the tubing connectors 22, 24, 26, 28, 30, 32, 34 and the openings 72, 74, 76, 78, 80, 82, 84 in the cassette cover portion 70 of the manifold or cassette assembly 50 will be color coded, a physical lock-out mechanism will not allow a tubing connector 20 to be misplaced in a hole in the cover portion 70 of the manifold or cassette assembly 50. The key interface between the shrouds 40 and the array of openings to match connectors 20 to the cover portion 70 of the manifold or cassette assembly 50 is designed so that fittings with common luer geometry are incapable of being connected to the wrong port in the cover portion of the manifold or cassette assembly 50.

By utilizing a varying number of key tabs and varying sizes of key tabs, a misconnection of common luer geometry interfaces is prevented. The geometry of the location and size of the tabs on each shroud portion 40 of each keyed connector 20 is reflected on the specific cassette port with a unique keyhole pattern. In addition, a stop system may be located in the body portion 90 of the manifold or cassette assembly 50 to prevent a keyed connector 20 from rotating more than about 60° after passing into the cassette assembly 50. The array of stops 92, 94 as shown in FIG. 4C and FIG. 5 are positioned in the body portion 90 of the manifold or cassette assembly 50 around the tubular openings 95 to physically contact the protrusions or tabs on each shroud 40 once the connector is rotated about 60° in a clockwise manner. The height of the stops 92, 94 can be established by the length of the shroud and/or the location of the tabs on each individual keyed connector 20.

The interface between the manifold or cassette assembly 50 and the individual keyed connectors 20 also provides a method for securely pre-connecting the desired set of connectors 20 to the manifold or cassette assembly 50 for shipping. Such pre-connection of the desired set of connectors 20 further minimizes errors and reduces set-up time at a patient care facility.

The shroud portion 40 of each individual keyed connector 20 is sized to have a length which prevents touching of the recessed luer fitting 45 within each connector 20 so that each luer fitting 45 will remain aseptic. As previously indicated, the diameter and the length of each shroud 40 may also function as a physical key feature along with the tabs on each connector 20 to provide another way of making the individual keyed connectors 20 unique.

Removing each connector 20 requires about a 60° counter clock wise turn and axial removal. Turning of each connector is facilitated by a pair of wings 33 on the top portion of each connector 20. A flange 35 both separates the top portion 31 of each keyed connector 20 from the shroud 40 and limits the depth of insertion of each keyed connector 20 into the cassette assembly 50.

Each individual keyed connector including a unique array of key features provides a repeatable method of applying and removing tubing sets from a cassette assembly 50 in a sterile manner. The key features on the bottom 43 of each shroud 40 of each individual keyed connector 20 and the stops 92 and 94 surrounding the tubular openings 95 in the cassette body 90 also provide a 60° positive engagement and mitigate the risk of the disconnection of the tubing sections from the manifold or cassette assembly 50 during shipment. The key features on each individual keyed connector 20 also provide a mechanism similar to the luer lock interface without the need to unscrew core pins when the luer connectors are molded.

Figure 6:
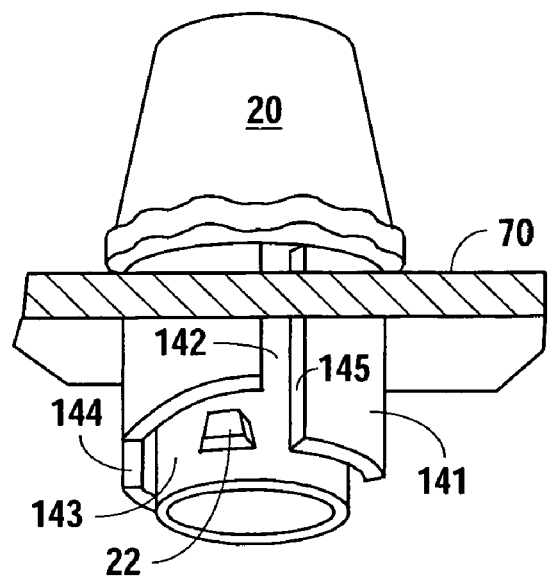
FIG. 6 is a perspective view of a first alternative of a shroud and skirted portal engagement.
Figure 7:
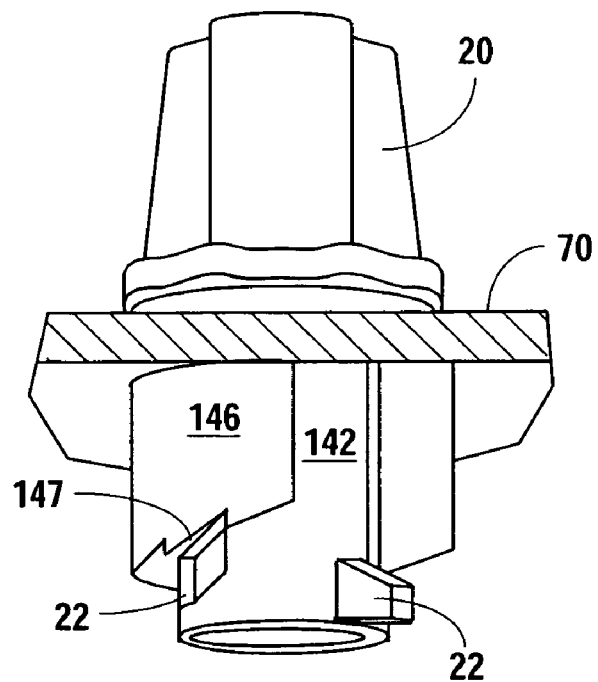
FIG. 7 is a perspective view of a second alternative of a shroud and skirted portal engagement including a ratchet mechanism.

As may be seen in FIG. 6 cassette cover portion 70 may be alternatively formed with a skirt 141 having slots 142 and openings 143 formed therein for allowing tabs 22 of connector 20 to access openings 143. Surfaces 144 and 145 of skirt 141 provide a rotation stop for tab 22. As shown in FIG. 7, cassette cover portion 70 may be alternatively formed with a skirt 146 having a stepped engagement ramp 147 that acts as a ratchet mechanism for tabs 22 when connector 20 is rotated with respect to manifold or cassette assembly 50. An audible click preferably occurs when tabs 22 engage each step of ramp 147.

While the disclosed connector to cassette assembly interface system has been disclosed according to its preferred and alternate embodiments, those of ordinary skill in the art will understand that numerous other embodiments have been enabled by the foregoing disclosure. Such other embodiments shall be included within the scope and meaning of the appended claims.

What is claimed is:

1. A connector to cassette assembly interface system comprising:
    a cassette assembly, said cassette assembly including:
        a cassette cover and a cassette body constructed and arranged to fit together to have a space therebetween;
    said cassette cover including a plurality of portals formed therein, each of said portals including a skirt portion extending from the bottom of said cassette cover into said space between said cassette cover and said cassette body;
    said cassette body including a plurality of tubular openings constructed and arranged to align with said portals in said cassette cover;
    a plurality of connectors having an upper portion and a lower portion, wherein said lower portion includes a luer fitting surrounded by a shroud, said shroud having a unique exterior surface configuration; and
    said skirt portion of said portal including a pattern of unique openings constructed and arranged to engage one of said plurality of connectors.

2. The connector to cassette interface system as defined in claim 1 wherein said unique exterior surface configuration includes the size and shape of said shroud.

3. The connector to cassette interface system as defined in claim 2 wherein the size and shape of said shroud is dependent on the sex and shape of said luer fitting.

4. The connector to cassette interface system as defined in claim 1 wherein said unique exterior surface configuration of said shroud includes one or more tabs extending from said shroud.

5. The connector to cassette interface system as defined in claim 4 wherein said unique exterior surface configuration comprises a size of said tabs.

6. The connector to cassette interface system as defined in claim 1 wherein said upper portion of each of said connectors includes at least one wing for facilitating rotation of said connectors.

7. The connector to cassette interface system as defined in claim 1 wherein each of said plurality of tubular openings includes a unique pattern of stops arranged around said tubular opening to engage extensions from said unique exterior surface configuration and to limit rotation of said connector after said connector has been inserted through said cassette cover.

8. The connector to cassette interface system as defined in claim 1 wherein each of said skirt portions includes an opening with a surface that limits rotation of said connector after said connector has been inserted through said cassette cover.

9. A cassette for engagement with a connector having a lower portion which includes a luer fitting surrounded by a shroud, said shroud having a unique diameter and a unique array of tabs extending therefrom, said cassette comprising:
    a cassette cover, said cassette cover having a plurality of portals formed thereon, each of said portals characterized by a skirt portion having a unique size and a unique array of openings formed therein; and
    a cassette body having a plurality of tubular openings formed therein said tubular openings being constructed and arranged to align with said portals when said cassette cover is placed on said cassette body;
    whereby each portal on said cassette cover is keyed to a single connector and wherein said skirt portion includes a stepped ramp.

10. The cassette as defined in claim 9 wherein said stepped ramp is for engagement with one of said tabs.

11. The cassette as defined in claim 9 wherein said cassette body further comprises an array of stops formed around said tubular openings.

12. The cassette as defined in claim 11 wherein said array of stops surrounding each tubular opening is positioned to engage the tabs.

13. The cassette as defined in claim 12 wherein said stops have different heights constructed and arranged to engage shrouds of different lengths.

14. The cassette as defined in claim 9 wherein said skirt portions each have an opening with a surface that limits a rotation of said connector after said connector has been inserted into said cassette.

15. A method for preventing mismatch of a set of connectors with a set of portals formed in a cassette, said method comprising the steps of:

forming each portal with a depending skirt, said depending skirt having a size and a pattern of opening therearound different from the other portals formed in the cassette; and forming a connector having a size and a pattern of protrusions therearound to engage one of the portal;

wherein each connector is rotated by manual engagement of a set of win

16. The method as defined in claim 15 wherein each connector is extending from said connector. is formed to have a shroud surrounding a luer fitting.

* * * * *

UNITED STATES PATENT AND TRADEMARK OFFICE
CERTIFICATE OF CORRECTION

PATENT NO. : 7,484,769 B2  
APPLICATION NO. : 11/487842  
DATED : February 3, 2009  
INVENTOR(S) : Domash et al.

Page 1 of 1

It is certified that error appears in the above-identified patent and that said Letters Patent is hereby corrected as shown below:

Col. 6, ln. 42, delete "therein" and insert --therein,--.
Col. 7, ln. 2, delete "opening" and insert --openings--.
Col. 7, ln. 6, delete "portal" and insert --portals--.
Col. 8, ln. 2, delete "win" and insert --wings extending from said connector.--.
Col. 8, ln. 4, delete "is extending from said connector.".

Signed and Sealed this

Sixteenth Day of June, 2009

JOHN DOLL  
*Acting Director of the United States Patent and Trademark Office*